(12) United States Patent
Fu et al.

(10) Patent No.: US 11,413,067 B2
(45) Date of Patent: Aug. 16, 2022

(54) PUNCTURING DEVICE AND ANCHORING DEVICE

(71) Applicant: LIFETECH SCIENTIFIC (SHENZHEN) CO., LTD, Shenzhen (CN)

(72) Inventors: Weiguo Fu, Shenzhen (CN); Mingyang Cai, Shenzhen (CN); Gang Wang, Shenzhen (CN); Xinjiong Qiu, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 371 days.

(21) Appl. No.: 16/477,970

(22) PCT Filed: Dec. 19, 2017

(86) PCT No.: PCT/CN2017/117111
§ 371 (c)(1),
(2) Date: Jul. 15, 2019

(87) PCT Pub. No.: WO2018/145518
PCT Pub. Date: Aug. 16, 2018

(65) Prior Publication Data
US 2020/0121363 A1 Apr. 23, 2020

(30) Foreign Application Priority Data

Feb. 7, 2017 (CN) .......................... 201710066957.X (51) Int. Cl.
*A61B 17/34* (2006.01)
(52) U.S. Cl.
CPC .. *A61B 17/3496* (2013.01); *A61B 2017/3486* (2013.01)

(58) Field of Classification Search
CPC .... A61B 2017/3425; A61B 2017/3486; A61B 17/3496
See application file for complete search history.

(56) References Cited

U.S. PATENT DOCUMENTS

| 4,976,710 A | 12/1990 | Mackin |
| 2003/0199852 A1 | 10/2003 | Seward et al. |

(Continued)

FOREIGN PATENT DOCUMENTS

| CN | 102302378 A | 1/2012 |
| CN | 203138744 U | 8/2013 |

(Continued)

OTHER PUBLICATIONS

International Search Report dated Mar. 15, 2018 in corresponding International application No. PCT/CN2017/117111; 4 pages.

(Continued)

*Primary Examiner* — Nicholas W Woodall
(74) *Attorney, Agent, or Firm* — Maier & Maier, PLLC (57) ABSTRACT

A puncturing device and an anchoring device, the puncturing device including: a puncturing needle, an inflatable anchoring balloon, and a catheter which passes through a proximal end and distal end of the anchoring balloon, the puncturing needle being movably accommodated within the catheter; in a filled state, a central area of an end portion of the distal end of the anchoring balloon is depressed towards the proximal end to form a depressed area, and a distal end of the catheter is located within the depressed area. The anchoring device includes the anchoring balloon and the catheter. The puncturing device may improve the accuracy and success rate of puncturing, and after puncturing is complete, an expansion balloon may be transported along a guide wire to expand a puncturing opening by simply withdrawing the puncturing needle and a push rod.

16 Claims, 9 Drawing Sheets

(56) References Cited

U.S. PATENT DOCUMENTS

| | | | |
|---|---|---|---|
| 2005/0056292 A1* | 3/2005 | Cooper | A61B 18/1492 128/898 |
| 2005/0124977 A1 | 6/2005 | Gonzalez et al. | |
| 2008/0103441 A1* | 5/2008 | Melsheimer | A61B 17/0401 604/96.01 |
| 2008/0172033 A1* | 7/2008 | Keith | A61B 1/018 604/506 |
| 2009/0125097 A1 | 5/2009 | Bruszewski et al. | |
| 2009/0264821 A1 | 10/2009 | Mafi et al. | |
| 2011/0172690 A1* | 7/2011 | Cohn | A61B 17/32053 606/170 |
| 2011/0245751 A1 | 10/2011 | Hofmann | |
| 2014/0121658 A1* | 5/2014 | Cosman, Jr. | A61B 18/1477 606/33 |
| 2014/0257203 A1 | 9/2014 | Favier et al. | |

FOREIGN PATENT DOCUMENTS

| | | |
|---|---|---|
| CN | 103349575 A | 10/2013 |
| CN | 105902326 A | 8/2016 |
| CN | 205494094 U | 8/2016 |
| CN | 106333766 A | 1/2017 |
| EP | 1498085 A1 | 1/2005 |
| EP | 1 820 436 A2 | 8/2007 |
| EP | 2 594 212 A2 | 5/2013 |
| EP | 2 801 325 A1 | 11/2014 |
| JP | 2016168228 A | 9/2016 |
| WO | 2006/062996 A2 | 6/2006 |
| WO | 2010/078196 A1 | 7/2010 |
| WO | 2016/183220 A1 | 11/2016 |

OTHER PUBLICATIONS

Office Action dated Apr. 12, 2019 in corresponding Chinese application No. 201710066957.X; 19 pages.
Indian Office Action dated Feb. 23, 2021, in connection with corresponding IN Application No. 201917033618; 6 pages.
Extended European Search Report dated Jan. 28, 2021, in connection with corresponding EP Application No. 17895957.3; 24 pages.
Office Action dated Nov. 25, 2021, in connection with corresponding European Application No. 17 895 957.3; 5 pages.

* cited by examiner

Fig.8i

PUNCTURING DEVICE AND ANCHORING DEVICE

FIELD

The present application relates to the field of interventional medical devices, and more particularly relates to a puncturing device and an anchoring device.

BACKGROUND

Use of a covered stent in a special lesion locus, such as an aortic arch, a coeliac trunk, bilateral renal arteries or a superior mesenteric artery, may affect the blood supply of an arterial branch vessel. The covered stent is subjected to in-situ fenestration in the surgical procedure by an energy or mechanical method to produce an expected hole, and then a branch stent is delivered to this hole to abut with the covered stent, so as to overcome the dependency of a treatment solution on an anatomical structure of a human branch vessel.

However, an existing mechanical fenestration device has the following defects: (1) when a puncturing needle is in contact with a coating membrane of the stent, the coating membrane may be sunken into the stent due to its flexibility to possibly cause the puncturing needle to bend or slide on the surface of the coating membrane; and (2) when the coating membrane is sunken into the stent under an acting force of the puncturing needle, a distance between the distal end of the puncturing needle and the contralateral coating membrane and a distance between the distal end of the puncturing needle and the vascular wall are extremely short, so that if an operator exerts an extremely high puncturing force, the puncturing needle would still continuously move forwards after making a puncturing success, which results in a relatively high possibility that the puncturing needle punctures the contralateral coating membrane or the vascular wall.

SUMMARY

One of the objectives of the present application is to provide a puncturing device which may prevent a puncturing needle from moving radially during puncturing and improve the puncturing accuracy and success rate, and may prevent a coating membrane from being sunken into a stent during puncturing, so as to prolong a distance between the distal end of the puncturing needle and a contralateral coating membrane or a vascular wall and reduce the possibility of damage to the contralateral coating membrane or the vascular wall.

Another objective of the present application is to provide an anchoring device which may keep a puncturing needle from moving radially after being expanded and improve the puncturing accuracy and success rate, and may prevent a coating membrane from being sunken into a stent during puncturing, so as to prolong a distance between the distal end of the puncturing needle and a contralateral coating membrane or a vascular wall and reduce the possibility of damage to the contralateral coating membrane or the vascular wall.

The present application provides a puncturing device, including a puncturing needle, an inflatable anchoring balloon and a catheter passing through a proximal end and a distal end of the anchoring balloon. The puncturing needle is movably arranged in the catheter. In a filled state, a central region of the distal end part of the anchoring balloon is sunken towards the proximal end to form a sunken region, and a distal end of the catheter is located in the sunken region.

In one embodiment, an axial length of the anchoring balloon ranges between 5 mm and 20 mm.

In one embodiment, a distance between the distal end of the anchoring balloon and the distal end of the catheter along an axial direction of the catheter is less than or equal to 2 mm.

In one embodiment, the catheter is a multi-cavity tube having at least two cavities. The multi-cavity tube includes an accommodating cavity and a filling cavity. The accommodating cavity axially passes through the anchoring balloon, and the puncturing needle is movably accommodated in the accommodating cavity. A distal end of the filling cavity is accommodated in the anchoring balloon, and a tube cavity of the filling cavity is communicated with an inside of the anchoring balloon.

In one embodiment, a hardness of a part, covered by the anchoring balloon, of the catheter is lower than that of the other part of the catheter.

In one embodiment, a length of the needle tip of the puncturing needle is less than or equal to 7 mm.

In one embodiment, the puncturing device further includes a handle connected with the puncturing needle. The handle includes a proximal end handle part and a distal end handle part which are opposite to each other. The proximal end handle part includes a proximal end handle shaft having an axial inner cavity and a proximal end handle ring connected to a side wall of the proximal end handle shaft. The axial inner cavity of the proximal end handle shaft passes through a proximal end face and a distal end face of the proximal end handle shaft. The distal end handle part includes a distal end handle shaft having an axial inner cavity and a distal end handle ring connected to the side wall of a distal end handle shaft. The axial inner cavity of the distal end handle shaft passes through a proximal end face and a distal end face of the distal end handle shaft. The proximal end handle shaft is movably arranged in the axial inner cavity of the distal end handle shaft in a penetrating manner, and the distal end handle ring is closer to a proximal end of the puncturing needle than the proximal end handle ring.

In one embodiment, an outer profile of the part, accommodated in the axial inner cavity of the distal end handle shaft, of the proximal end handle shaft on a section perpendicular to an axial direction of the proximal end handle shaft is noncircular.

In one embodiment, the handle further includes a fastener arranged at a distal end of the distal end handle shaft and connected with a proximal end of the anchoring assembly.

In one embodiment, the puncturing device further includes a push rod connected between the puncturing needle and the handle, and a proximal end of the push rod is fixedly accommodated in the axial inner cavity of the proximal end handle shaft.

In one embodiment, the push rod further includes a reinforcing tube arranged on the push rod. The reinforcing tube is arranged on the rod-like part, close to the proximal end of the push rod, of the push rod in a sleeving manner, and a hardness of the reinforcing tube is higher than that of the rod-like part, close to the proximal end of the push rod, of the push rod.

In one embodiment, an axial length of the reinforcing tube is less than or equal to ⅓ of an axial length of the push rod.

The present application further provides an anchoring device, including an inflatable anchoring balloon and a catheter passing through a proximal end and a distal end of the anchoring balloon. In a filled state, a central region of the distal end part of the anchoring balloon is sunken towards the proximal end to form a sunken region, and a distal end of the catheter is located in the sunken region.

In one embodiment, an axial length of the anchoring balloon ranges between 5 mm and 20 mm.

In one embodiment, a distance between the distal end of the anchoring balloon and the distal end of the catheter along an axial direction of the catheter is less than or equal to 2 mm.

In one embodiment, a hardness of a part, covered by the anchoring balloon, of the catheter is lower than that of the other part of the catheter.

Compared with the prior art, the present application at least has the following beneficial effects that:

(1) according to the puncturing device provided by the present application, the puncturing needle is threaded out from the distal end of the anchoring balloon; after the anchoring balloon is filled to expand, the radial movement of the puncturing needle may be restrained to achieve higher puncturing accuracy and higher success rate;

(2) according to the puncturing device provided by the present application, after the anchoring balloon is filled to expand, the central region of the distal end part of the anchoring balloon has a sunken region sunken from the distal end to the proximal end, and the distal end of the catheter is located in the sunken region; in an in-situ fenestration process of a covered stent, the distal end part of the catheter abuts against a coating membrane of the punctured stent, and the elastic coating membrane is stressed by a pull force to form a tension region, surrounded by the distal end face of the anchoring balloon, on the coating membrane; after the puncturing needle is threaded out from the distal end of the anchoring balloon and in contact with the coating membrane of this tension region, the coating membrane of the tension region is directly punctured by the puncturing needle instead of being sunken into the stent, so that the puncturing success rate is increased; furthermore, as the coating membrane in the tension region may not be sunken into the stent, the distance between the distal end of the puncturing needle and the contralateral coating membrane and the distance between the distal end of the puncturing needle and the vascular wall are prolonged, and then the possibility that the puncturing needle still continuously moves forwards after making a puncturing success under the extremely high puncturing force to puncture the contralateral coating membrane or the vascular wall is reduced; and (3) according to the anchoring device provided by the present application, the anchoring balloon may keep the puncturing needle from moving radially after being expanded to improve the puncturing accuracy and success rate; and furthermore, as the central region of the distal end part of the anchoring balloon has the sunken region sunken from the distal end to the proximal end, the distal end face of the anchoring balloon abuts against the coating membrane of the punctured stent in the in-situ fenestration process of the covered stent to prevent the coating membrane from being sunken into the stent during puncturing, which prolongs the distance between the distal end of the puncturing needle and the contralateral coating membrane or the vascular wall and then reduces the possibility of damage to the contralateral coating membrane or the vascular wall.

BRIEF DESCRIPTION OF THE DRAWINGS

FIGS. 8a to 8i are schematic diagrams of a method of in-situ fenestration for a thoracic aorta covered stent by using the puncturing device of FIG. 1 in an aortic dissection treatment process, where

DETAILED DESCRIPTION

To make the objectives, technical solutions and advantages of the present application clearer, the present application is further described below in detail in combination with accompanying drawings and embodiments. It should be understood that the specific embodiments described herein are merely explanatory of the present application, and are not intended to limit the present application.

To describe the structure of a puncturing device more clearly, terms "proximal end" and "distal end" are defined herein as commonly used terms in the interventional medical field. Specifically, the "distal end" refers to the end away from an operator in an operation process, and the "proximal end" refers to the end close to the operator in the operation process.

Unless otherwise defined, all technical and scientific terms used in the present application have the same meanings as generally understood by those skilled in the art of the present application. The terms used in the description of the present application are only used to describe the specific embodiments, and are not intended to limit the present application.

Figure 1:
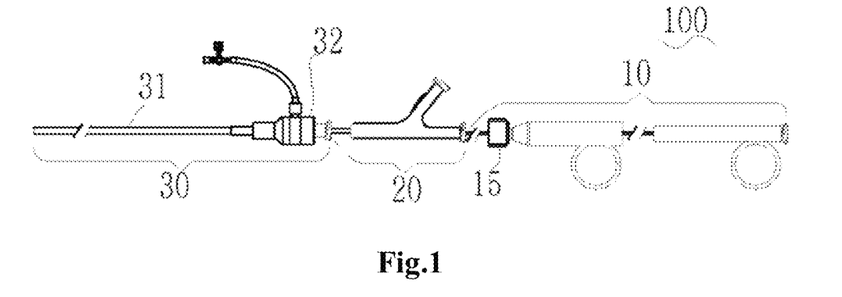
FIG. 1 is a front view of a puncturing device of an embodiment of the present application, the puncturing device including a puncturing assembly, an anchoring assembly and a delivery assembly.

Referring to FIG. 1, a puncturing device 100 provided by the embodiment of the present application is used for in-situ fenestration of a covered stent. The puncturing device 100 includes: a puncturing assembly 10, an anchoring assembly 20 and a delivery assembly 30. The anchoring assembly 20 may be fixedly connected with the puncturing assembly 10 and detachably connected with the delivery assembly 30, or the anchoring assembly 20 may be detachably connected with both the puncturing assembly 10 and the delivery assembly 30. Regardless of the connection mode of the three assemblies, the distal end of a puncturing needle of the puncturing assembly 10 may pass through the anchoring assembly 20, move in the delivery assembly 30 and extend out of the distal end of the delivery assembly 30 under the pushing of an external force once the three assemblies are assembled together.

Figure 2:
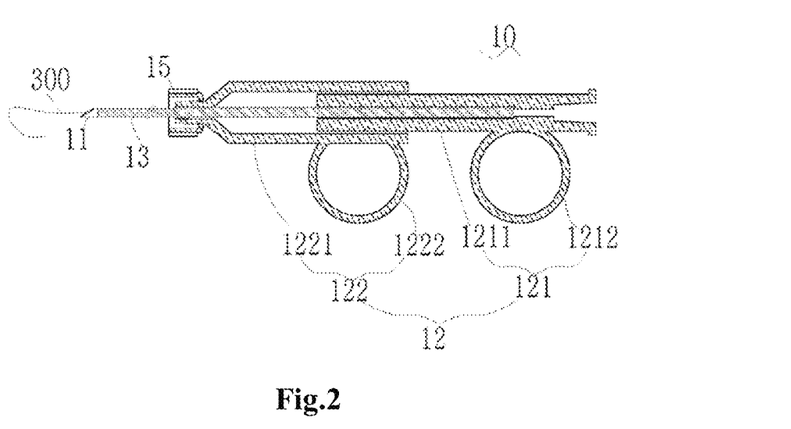
FIG. 2 is a schematic diagram of the puncturing assembly in FIG. 1, the puncturing assembly including a puncturing needle, a handle and a push rod connected between the puncturing needle and the handle.

Referring to FIG. 2, the puncturing assembly 10 includes a puncturing needle 11, a handle 12 and a flexible push rod 13. The proximal end of the puncturing needle 11 is connected with the handle 12 through the push rod 13. The puncturing needle 11 and the push rod 13 both have mutually communicated inner cavities. A guide wire 300 is movably arranged in the inner cavities of the puncturing needle 11 and the push rod 13 in a penetrating manner.

Figure 3:
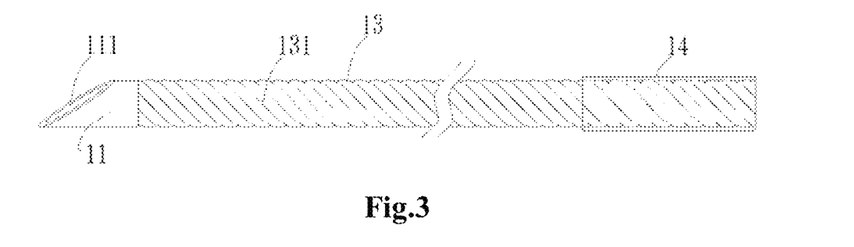
FIG. 3 is a schematic diagram of the puncturing needle and the push rod in FIG. 2.

Referring to FIG. 3 together, the puncturing needle 11 is a hollow needle-like object having an inner cavity. The distal end of the puncturing needle 11 has at least one distal end slope 111 inclined relative to an axial direction of the puncturing needle 11, and may puncture a coating membrane of a covered stent. In the present embodiment, the puncturing needle 11 is a disposable sterile injection needle. It can be understood that in other embodiments, the puncturing needle 11 also may be a Touhy needle, a Franseen needle, a Whitacre needle, a Cournand needle, a Mengini needle, a Backcut Bevel needle, or the like, as long as it is the hollow needle-like object having the inner cavity and its distal end may puncture the coating membrane. The diameter of the inner cavity of the puncturing needle 11 is greater than or equal to 0.36 mm so as to allow the guide wire 300 to pass through it successfully. The length of the needle tip of the puncturing needle 11 is less than or equal to 7 mm so as to ensure that the puncturing needle 11 does not damage the vascular wall in a delivery process and may pass through a bent part of a blood vessel more smoothly.

Figure 4A:
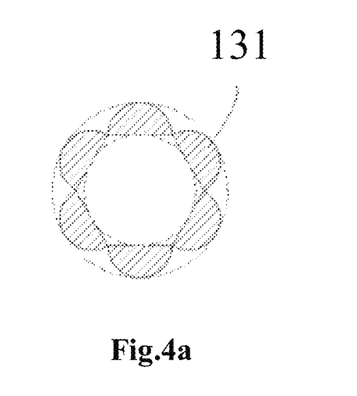
FIG. 4a is a are sectional view of an embodiment of the push rod in FIG. 2 on a section perpendicular to an axial direction.
Figure 4B:
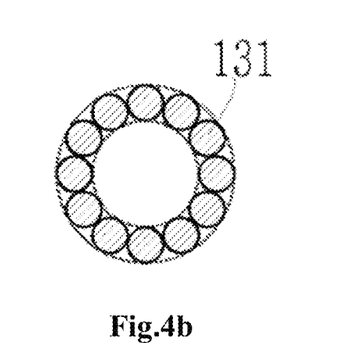
FIG. 4b is a are sectional view of an embodiment of the push rod in FIG. 2 on a section perpendicular to an axial direction.
Figure 4C:
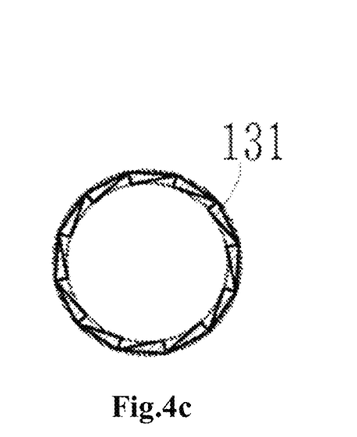
FIG. 4c is a are sectional view of an embodiment of the push rod in FIG. 2 on a section perpendicular to an axial direction.
Figure 4D:
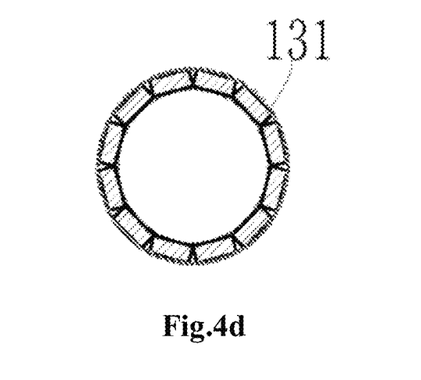
FIG. 4d is a are sectional view of an embodiment of the push rod in FIG. 2 on a section perpendicular to an axial direction.

The push rod 13 has a hollow spiral tubular structure having an inner cavity, may be twisted by a single or multiple wires 131, and has good flexibility and fracture resistance. The push rod 13 of this structure may comply with blood vessels in different degrees of bending to smoothly pass through the bent part of the blood vessel and guarantee no damage to the vascular wall in the delivery process. The diameter of the inner cavity of the push rod 13 is more than or equal to 0.36 mm so as to allow the guide wire 300 to pass through it successfully. In the present embodiment, the push rod 13 is twisted by 6 metal wires (referring to FIG. 4a). It can be understood that in other embodiments, the push rod 13 also may be made of a macromolecular material. It can be further understood that in other embodiments, the push rod also may be twisted by 12 metal wires (referring to FIG. 4b). It can be further understood that in other embodiments, the push rod also may be twisted by multiple metal wires having triangular sections (referring to FIG. 4c) or multiple metal wires having rectangular sections (referring to FIG. 4d).

In the present embodiment, a reinforcing tube 14 is also arranged on a rod-like part, close to the proximal end of the push rod 13, of the push rod 13 in a sleeving manner. The hardness of the reinforcing tube 14 is higher than that of the rod-like part, close to the proximal end of the push rod 13, of the push rod 13. The proximal end of the reinforcing tube 14 is fixedly accommodated in an inner cavity of the handle 12. The hardness of a material of the reinforcing tube 14 is higher than that of the material, close to the proximal end of the push rod 13, of the push rod 13, so that the pushing force of the distal end of the push rod 13 may be increased due to the existence of the reinforcing tube 14, and the defect that the rod-like part, close to the proximal end of the push rod 13, of the push rod 13 bends to deform easily is avoided. In addition, the reinforcing tube 14 is more favorable for transmission of the pushing force after being driven by the handle 12, so that a higher puncturing force may be provided for the puncturing needle 11 to increase the success rate of puncturing the coating membrane of the covered stent. The axial length of the reinforcing tube 14 is less than or equal to ⅓ of the axial length of the push rod 13 so as to ensure that the reinforcing tube 14 does not affect the flexibility of the rod-like part, close to the distal end of the push rod 13, of the push rod 13. A connection between the reinforcing tube 14 and the outer surface of the rod-like part, close to the proximal end, of the push rod 13 may be implemented by a technical measure commonly used by those skilled in the art, such as welding, adhesion, riveting or screwing. It can be understood that in other embodiments, the reinforcing tube 14 also may be connected with the proximal end of the rod-like part, close to the proximal end, of the push rod 13 by the technical measure commonly used by those skilled in the art, such as welding, adhesion, riveting or screwing. It can be further understood that in other embodiments, part or the whole of the outer surface the rod-like part, close to the proximal end, of the push rod 13 also may be coated, sprayed or electroplated with one or multiple layers of a material to form a reinforcing sheet or reinforcing tube with higher hardness. The hardness of the material is higher than that of the rod-like part, close to the proximal end of the push rod 13, of the push rod 13. It can be further understood that in other embodiments, a metal wire or a macromolecular wire may be prepared from the material having the hardness higher than that of the rod-like part, close to the proximal end of the push rod 13, of the push rod 13 at first; then the single or multiple metal wires or macromolecular wires are twisted to form the reinforcing tube, and the reinforcing tube is connected with the proximal end of the rod-like part, close to the proximal end, of the push rod 13. It can be further understood that the push rod 13 also may be twisted by the single or multiple wires having the hardness gradually improved from the proximal end to the distal end, so that the hardness of the part, close to the proximal end, of the push rod 13 formed thereby is higher than that of the part close to the distal end, and at the moment, the reinforcing tube or the reinforcing sheet may be omitted. All of the above-mentioned implementation modes may achieve the goals of increasing the pushing force of the distal end of the push rod 13 and avoiding easy bending deformation of the rod-like part close to the proximal end of the push rod 13.

It can be understood that in other embodiments, the push rod 13 also may not include the reinforcing tube 14 as long as the push rod 13 is of the hollow spiral tubular structure having the inner cavity and its inner cavity is communicated with the inner cavity of the puncturing needle 11 to transmit the pushing force to the puncturing needle 11 to allow the puncturing needle 11 to puncture the coating membrane of the covered stent. It can be understood that the number, the shapes, the material or the wire diameters (as shown in FIGS. 4a to 4d) of the multiple wires 131 may be adjusted according to an actual requirement or need so as to allow the push rod 13 to have different hardness and flexibilities to adapt to different anatomical structures.

Referring to FIG. 2 again, the handle 12 is a one-hand operation handle, and includes a proximal end handle part 121 and a distal end handle part 122 which are opposite to each other. The proximal end handle part 121 includes a proximal end handle shaft 1211 having an axial inner cavity and a proximal end handle ring 1212 perpendicularly connected to the side wall of the proximal end handle shaft 1211. The axial inner cavity of the proximal end handle shaft 1211 passes through the proximal end face and the distal end face of the proximal end handle shaft 1211. The distal end handle part 122 includes a distal end handle shaft 1221 having an axial inner cavity and a distal end handle ring 1222 perpendicularly connected to the side wall of the distal end handle shaft 1221. The axial inner cavity of the distal end handle shaft 1221 passes through the proximal end face and the distal end face of the distal end handle shaft 1221. The proximal end handle shaft 1211 is movably arranged in the axial inner cavity of the distal end handle shaft 1221 in a penetrating manner, and the distal end handle ring 1222 is closer to the proximal end of the puncturing needle 11 than the proximal end handle ring 1212. Therefore, the proximal end handle ring 1212 may be allowed to do axial motion relative to the distal end handle ring 1222 to drive the proximal end handle shaft 1211 to do axial motion relative to the distal end handle shaft 1221 through opening and closing of an index finger and a thumb of one hand, as long as an operator puts the index finger and the thumb of one hand into the distal end handle ring 1222 and the proximal end handle ring 1212 respectively.

The outer profile of the part, accommodated in the axial inner cavity of the distal end handle shaft 1221, of the proximal end handle shaft 1211 on a section perpendicular to the axial direction of the proximal end handle shaft 1211 is noncircular, and the axial inner cavity of the distal end handle shaft 1221 has a noncircular inner profile cooperating with the noncircular outer profile, so that when the proximal end handle shaft 1211 axially moves relative to the distal end handle shaft 1221, the noncircular outer profile cooperates with the noncircular inner profile to ensure that the proximal end handle shaft 1211 only axially moves instead of easily circumferentially deviating or sliding relative to the distal end handle shaft 1221, and the puncturing accuracy is improved.

The distal end of the distal end handle shaft 1221 is provided with a hollow fastener 15. The proximal end of the fastener 15 is fixedly connected with the outer surface of the distal end of the distal end handle shaft 1221 by a technical measure commonly used in the art, such as adhesion, screwing, riveting, hot melting or welding. The distal end of the fastener 15 has an internal thread and may be detachably connected with the proximal end of the anchoring assembly 20 through the thread.

The proximal end of the push rod 13 is fixedly accommodated in the axial inner cavity of the proximal end handle shaft 1211. The distal end of the push rod 13 is threaded out of the distal end of the distal end handle shaft 1221 through the axial inner cavity of the distal end handle shaft 1221 and is connected with the puncturing needle 11. Therefore, during the axial motion relative to the distal end handle shaft 1221, the proximal end handle shaft 1211 drives the push rod 13 to also axially move in the same moving direction of the proximal end handle shaft 1211 relative to the distal end handle shaft 1221 and drives the puncturing needle 11 connected with the push rod 13 to move towards the distal end or the proximal end.

Figure 5A:
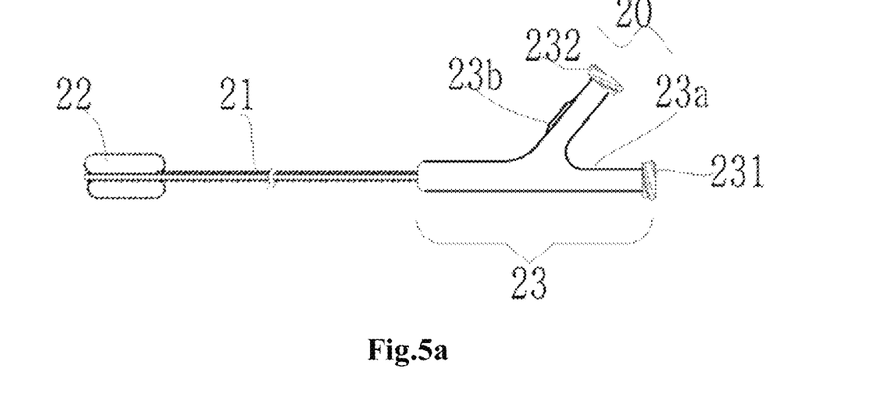
FIG. 5a is a schematic diagram of a front view of the anchoring assembly in FIG. 1, the anchoring assembly including an anchoring balloon, a catheter and a catheter seat.
Figure 5B:
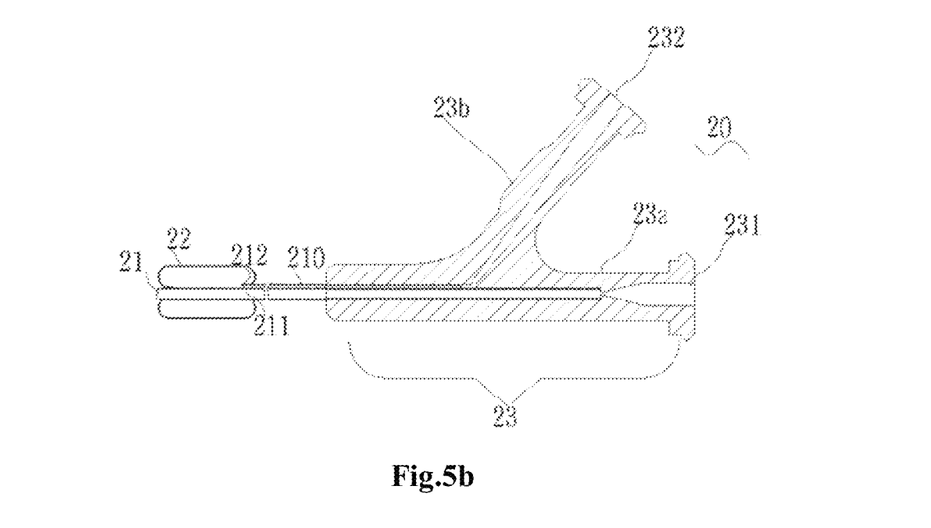
FIG. 5b is a schematic diagram of a sectional view of the anchoring assembly in FIG. 1 on a section parallel to the axial direction, the anchoring assembly including an anchoring balloon, a catheter and a catheter seat.
Figure 5C:
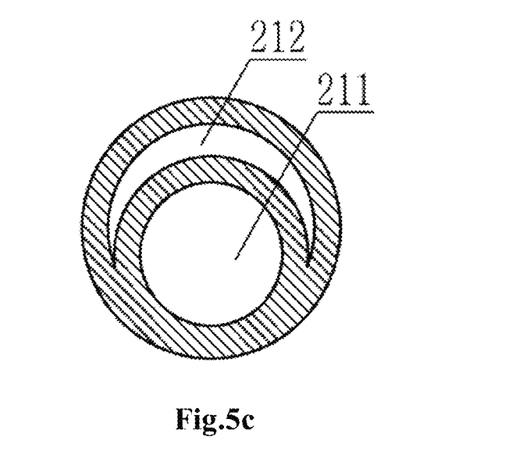
FIG. 5c is a schematic diagram of a sectional view of the catheter in FIG. 1 on a section parallel to the axial direction, the anchoring assembly including an anchoring balloon, a catheter and a catheter seat

Referring to FIG. 1 and FIG. 5a together, the anchoring assembly 20 includes a catheter 21, an inflatable anchoring balloon 22 arranged at the distal end of the catheter 21 and a catheter seat 23 arranged at the proximal end of the catheter 21. Referring to FIGS. 5a, 5b and 5c together, the catheter 21 is a double-cavity tube 210 passing through the proximal end and the distal end of the anchoring balloon 22. A distance between the distal end of the anchoring balloon 22 and the distal end of the catheter 21 in the axial direction of the catheter 21 is less than or equal to 2 mm. The double-cavity tube 210 includes an accommodating cavity 211 having an axial length and a filling cavity 212 approximately parallel to the accommodating cavity 211. The puncturing needle 11 may be preassembled in the catheter 21 by a manufacturer and sold as a whole, or may be only assembled in the catheter 21 by an operator before the surgery. Correspondingly, the puncturing needle 11 is movably arranged in the catheter 21, including a situation that the puncturing needle 11 is preassembled together with the catheter 21, but may move in the catheter 21 under the pushing of an external force, and a situation that the puncturing needle 11 moves relative to the catheter 21 when assembled into the catheter 21 by the operator.

The accommodating cavity 211 axially passes through the proximal end and the distal end of the anchoring balloon 22 and is used for movably accommodating the puncturing needle 11 and the push rod 13. (In other words, the puncturing needle 11 and the push rod 13 of the puncturing assembly 10 are movably arranged in the accommodating cavity 211 in a penetrating manner.) The distal end of the filling cavity 212 is accommodated in the anchoring balloon 22, and the tube cavity of the filling cavity 212 is communicated with the inside of the anchoring balloon 22 to provide a channel for allowing a liquid medium to flow into the anchoring balloon 22 through the filling cavity 212, so as to allow the anchoring balloon 22 to expand under the filling of the liquid medium flowing in through the filling cavity 212.

It can be understood that in other embodiments, the filling cavity 212 also may be arranged outside the accommodating cavity 211 and coaxial with the accommodating cavity 211 as long as the distal end of the filling cavity 212 is accommodated in the anchoring balloon 22 and the tube cavity of the filling cavity 212 is communicated with the inside of the anchoring balloon 22. The filling cavity 212 of this structure has a larger cross sectional area to increase the flow rate of the liquid medium within unit time and then shorten the filling and deflating time of the anchoring balloon 22.

It can be understood that the catheter 21 also may be a three-cavity tube, a four-cavity tube or a multi-cavity tube having more tube cavities as long as one tube cavity is used as the accommodating cavity 211 for movably accommodating the puncturing needle 11 and the push rod 13 and one tube cavity is used as the filling cavity 212 for providing the channel for allowing the liquid medium to flow into the anchoring balloon 22 through the filling cavity 212. Other tube cavities of the multi-cavity tube may be used as channels for other conventional treatment and diagnosis methods in the art, such as contrast medium injection, therapeutic agent injection or cryoablation.

In the present embodiment, the hardness of the part, covered by the anchoring balloon 22, of the catheter 21 is lower than that of the part, close to the proximal end and not covered by the anchoring balloon 22, of the catheter 21. In this way, the part (namely the distal end of the catheter 21), welded with the anchoring balloon 22, of the catheter 21 is softer and higher in compliance, deforms more easily along with the expansion of the anchoring balloon 22, and better complies with the bent anatomical structure of the blood vessel than the proximal end of the catheter 21. It can be understood that in other embodiments, the hardness of the distal end of the catheter 21 also may be the same as that of the proximal end of the catheter 21 as long as the distal end of the catheter 21 may deform along with the expansion of the anchoring balloon 22 to adapt to the bent structure of the blood vessel.

After being filled, the anchoring balloon 22 restrains the radial movement of the distal end of the catheter 21 and the radial movement of the part, covered by the anchoring balloon 22, of the catheter 21, so as to ensure that the push rod 13 located in the accommodating cavity 211 of the catheter 21 and the puncturing needle 11 connected with the push rod 13 do not move radially. It can be understood that in other embodiments, when the accommodating cavity 211 and the filling cavity 212 of the catheter 21 are coaxially arranged, the puncturing needle 11 and the push rod 13 of the puncturing assembly 10 are coaxial with the catheter 21 of the anchoring assembly 20. Furthermore, the anchoring balloon 22 of an axially symmetric structure is also coaxial with the puncturing needle 11, the push rod 13 and the catheter 21. Therefore, the anchoring balloon 22 may cling to the vascular wall after being filled at a target position to ensure that the puncturing needle 11 and the push rod 13 are located at the central axis of the blood vessel and do not move radially.

Figure 6:
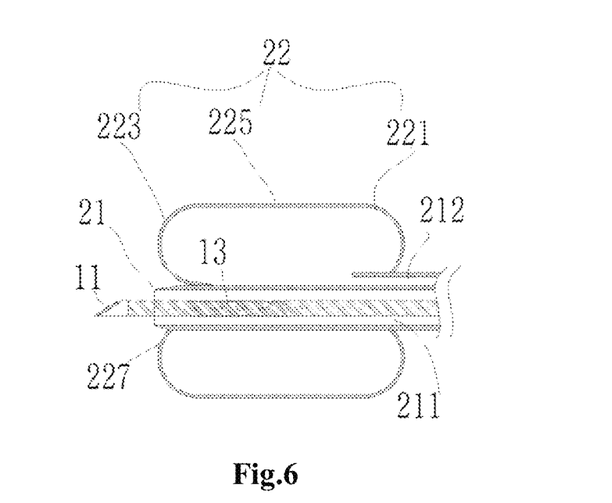
FIG. 6 is a schematic diagram of the puncturing needle and the push rod in FIG. 2 which are located in the anchoring balloon and the catheter in FIG. 5b.

Referring to FIG. 5b and FIG. 6 together, the main body of the anchoring balloon 22 is cylindrical and has a proximal end part 221 and a distal end part 223 which are opposite to each other and a main body part 225 located between the proximal end part 221 and the distal end part 223. In the filled state, the central region, close to the catheter 21, of the distal end part 223 of the anchoring balloon 22 forms a sunken region sunken from the distal end to the proximal end, thus the distal end part has a conical surface 227 sunken from the distal end to the proximal end and surrounding the catheter 21, and the distal end of the catheter 21 is located in the sunken region. In this way, the distal end face of the anchoring balloon 22 is an annular end face surrounding the catheter 21. When the anchoring balloon 22 is in the filled state, the distal end of the catheter 21 is located in the sunken region, that is, the distal end face of the catheter 21 is flush with the annular end face or is closer to the proximal end than the annular end face. After the anchoring balloon 22 is filled to expand in a target blood vessel, the annular end face of the distal end of the anchoring balloon 22 may abut against the coating membrane of the covered stent, and the elastic coating membrane is stressed by a pull force to form a tension region, surrounded by the distal end face of the anchoring balloon, on the coating membrane. After the puncturing needle 11 is threaded out from the distal end of the anchoring balloon 22 and in contact with the coating membrane of this tension region, the coating membrane in the tension region is directly punctured by the puncturing needle 11 instead of being sunken into the covered stent, so that the puncturing success rate is increased. In addition, as the coating membrane in the tension region may not be sunken into the covered stent, the distance between the distal end of the puncturing needle 11 and the contralateral coating membrane and the distance between the distal end of the puncturing needle 11 and the vascular wall are prolonged, and then the possibility that the puncturing needle 11 continuously moves forwards after making a puncturing success to puncture the contralateral coating membrane or the vascular wall is reduced.

It can be understood that in other embodiments, the conical surface 227 of the distal end part 223 of the anchoring balloon 22 also may be surfaces of other shapes sunken from the distal end to the proximal end, such as a cup shape, a bowl shape or a hemispherical shape. The main body of the anchoring balloon 22 also may be of other non-cylindrical shapes as long as the central region of the distal end of the anchoring balloon 22 is provided with the sunken region surrounding the distal end face of the catheter 21 to provide the pull force for the coating membrane and form the tension region.

In the present embodiment, the proximal end part 221 of the anchoring balloon 22 also has a surface sunken from the proximal end to the distal end, and this surface and the annular end face of the proximal end part 223 cooperate together to further restrain the radial movement of the puncturing needle 11.

The anchoring balloon 22 is a semi-compliable balloon. After arriving at the point to be punctured, the part, close to the distal end and covered by the anchoring balloon 22, of the catheter 21 may bend under the impact of the filled anchoring balloon 22 with the increase of the pressure in the anchoring balloon 22, so as to better comply with the bent anatomical structure of the blood vessel.

It can be understood that in other embodiments, the anchoring balloon 22 also may adopt a compliable balloon, and at the moment, the hardness of the part, covered by the anchoring balloon 22, of the catheter 21 is required to be lower than that of the filled anchoring balloon 22, so that after the anchoring balloon 22 is filled, the part, covered by the anchoring balloon 22, of the catheter 21 also may correspondingly bend to comply with the bent anatomical structure of the blood vessel.

The axial length of the anchoring balloon 22 preferably ranges between 5 mm and 20 mm so as to ensure that the main body part of the anchoring balloon 22 may not be located in a bent region of the target blood vessel. In this way, the anchoring balloon 22 may not be restrained by the space of the bent region after being filled with the liquid medium and may freely expand to be basically consistent with its filled shape in an external environment. Therefore, the relative positions between the puncturing needle 11 as well as the push rod 13 in the filled anchoring balloon 22 and the anchoring balloon 22 are also basically consistent with the relative positions between the puncturing needle 11 as well as the push rod 13 and the anchoring balloon 22 before the anchoring balloon 22 is filled, so as to avoid the deviation caused by incomplete filling of the anchoring balloon 22, and then the position of the puncturing needle 11 in the radial direction of the target blood vessel may be prejudged. Furthermore, the anchoring balloon 22 of an axially symmetric structure or an axially asymmetric structure is adopted to allow the puncturing needle 11 to be approximately aligned with the center of the punctured region. Preferably, in the present embodiment the axial length of the anchoring balloon 22 is 10 mm.

In the filled state, the distance between the distal end of the anchoring balloon 22 and the distal end of the catheter 21 along the axial direction of the catheter 21 is equal to or less than 2 mm, that is, the distal end of the catheter 21 is flush with the distal end of the anchoring balloon 22 or the distal end of the anchoring balloon 22 slightly extends out of the distal end of the catheter 21. This distance may ensure that the puncturing needle 11 may not puncture the anchoring balloon 22 when threaded out from the anchoring balloon 22 and does not affect the bendability of the distal end of the catheter 21. In addition, if the target blood vessel is curvy, the catheter 21 and the anchoring balloon 22 at the distal end of the catheter 21 may move forwards towards the distal end along the side, having a relatively large bending radius, of the target blood vessel, and at the moment, the axial direction, close to the distal end, of the catheter 21 is away from the central axis of the target blood vessel along the lengthwise direction of the target blood vessel. The distance between the distal end of the anchoring balloon 22 and the distal end of the catheter 21 along the axial direction of the catheter 21 is equal to or less than 2 mm, so that the filled anchoring balloon 22 generates a correction acting force towards the side, having a relatively small bending radius, of the target blood vessel on the part, close to the distal end, of the catheter 21, and the axial direction, close to the distal end, of the catheter 21 may be easily corrected by the anchoring balloon 22 to be close to the central axis of the target blood vessel along the lengthwise direction of the target blood vessel.

Referring to FIGS. 5a and 5b again, in the present embodiment, the catheter seat 23 is of a Y-shaped structure, and includes a hollow main body tube 23a and a hollow side branch tube 23b inclined relative to the main body tube 23a. The proximal end of the main body tube 23a of the catheter seat 23 is provided with an opening 231 communicated with the accommodating cavity 211 of the catheter 21 so as to allow the distal end of the puncturing needle 11 and the distal end of the push rod 13 to enter the accommodating cavity 211 of the catheter 21 in sequence through the opening 231. The proximal end of the side branch tube 23b of the catheter seat 23 is provided with a filling port 232 communicated with the filling cavity 212 of the catheter 21. The filling cavity 212 is connected with an external pressure device (not shown in the figure) through the filling port 232. The liquid medium in the external pressure device enters the anchoring balloon 22 through the filling port 232 and the filling cavity 212 in sequence to fill and expand the anchoring balloon 22.

It can be understood that in other embodiments, the catheter seat 23 also may be of a structure having three or more interfaces, and only one interface is communicated with the accommodating cavity 211 of the catheter 21, one interface is communicated with the filling cavity 212 of the catheter 21, and the other interface may be respectively connected to conventional diagnosis and treatment equipment such as external radiography equipment, infusion equipment or circulating equipment to implement conventional diagnosis and treatment methods such as real-time radiography, delivery of drugs or systemic circulation for a patient.

Referring to FIG. 5a and FIG. 1 together, the proximal end of the catheter seat 23 has an external thread and may be detachably connected with the internal thread of the fastener 15 of the puncturing assembly 10.

It should be noted that other components (such as a balloon protecting sheath arranged outside the anchoring balloon 22, a developing marker arranged on the catheter 21, a guide head (namely a tip head) arranged at the distal end of the catheter 21 and a Luer connector connected to one interface of the catheter seat 23) on the balloon catheter commonly used in the art also may be arranged on the anchoring assembly 20, and at the moment, the anchoring assembly 20 and other components arranged thereon may form an anchoring device. It should be further noted that other components (such as the balloon protecting sheath arranged outside the anchoring balloon 22, the developing marker arranged on the catheter 21, the guide head arranged at the distal end of the catheter 21 and the Luer connector connected to one interface of the catheter seat 23) on the balloon catheter commonly used in the art also may be parts of the anchoring assembly 20.

Figure 7A:
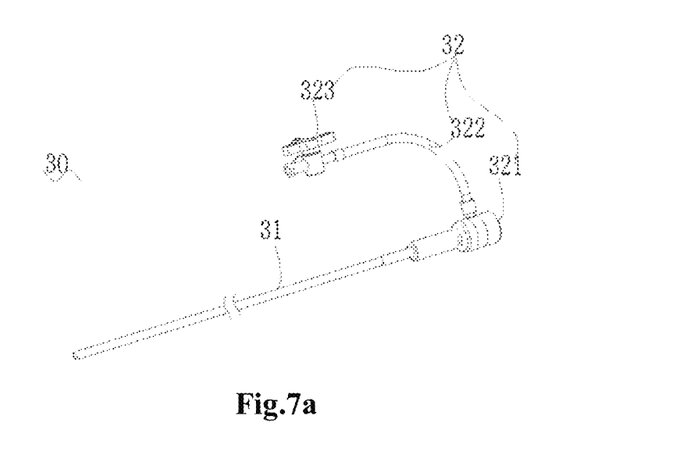
FIG. 7a is a schematic diagram of a front view of the delivery assembly in FIG. 1, the delivery assembly including a delivery sheath tube and a sheath tube seat.

Referring to FIG. 1 and FIG. 7a together, the delivery assembly 30 includes a delivery sheath tube 31 and a sheath tube seat 32 arranged at the proximal end of the delivery sheath tube 31. The sheath tube seat 32 includes a main body 321 connected with the delivery sheath tube 31 and a side tube 322 perpendicularly connected with the side wall of the main body 321. A hollow elastic sealing member (not shown in the figure) is arranged inside the main body 321. The sealing member is in close contact with the catheter 21 of the anchoring assembly 20 to prevent leakage of the blood from the periphery of the catheter 21. It can be understood that in other embodiments, the sealing member also may be an O-shaped ring or of other structures having pores as long as it may deform elastically to clasp the periphery of the catheter 21 to achieve a sealing effect. The distal end of the side tube 322 is provided with a valve body 323 connected with a Luer connector or an external infusion device. In the surgical procedure, air and blood may be discharged by unscrewing the Luer connector, or drugs may be injected through the external infusion device.

Figure 7B:
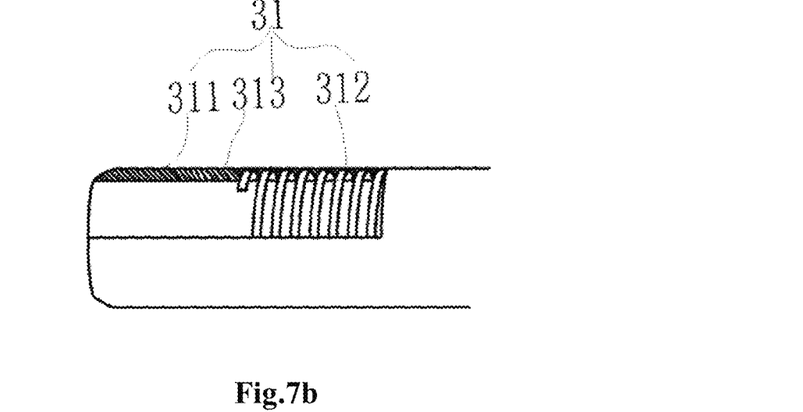
FIG. 7b is a schematic diagram of a partially enlarged sectional view of the delivery sheath tube of the delivery assembly in FIG. 1.

Referring to FIG. 7a and FIG. 7b together, the tube body of the delivery sheath tube 31 includes an external macromolecular layer 311, a metal reinforcing layer 312 and a PTFE (polytetrafluoroethylene) inner membrane layer 313 in sequence from outside to inside. The diameter of the delivery sheath tube 31 ranges between 2.0 mm and 6.0 mm so as to allow the catheter 21 of the anchoring assembly 20 to pass through it. Specifically, in the present embodiment, the diameter of the delivery sheath tube 31 is 4.0 mm.

A method for in-situ fenestration of the covered stent by using the puncturing device 100 of the first embodiment will be described below in detail.

By taking the surgery of treating an aortic dissection involving an arch and a left subclavian artery for example, the method specifically includes the following steps that:

First step: first, an incision is cut near a right groin of a patient to expose a right femoral artery.

Figure 8A:
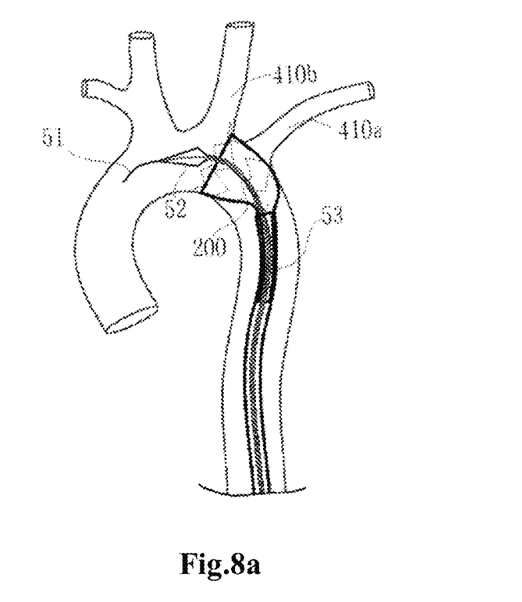
FIG. 8a is a schematic diagram of implanting the thoracic aorta covered stent, partially releasing the thoracic aorta covered stent and covering the blood inflow end of a left subclavian artery.

Referring to FIG. 8a, under the guidance of a stent delivery guide wire 51 and a guide head 52 of a thoracic aorta stent deliverer, a thoracic aorta covered stent 200 (hereinafter referred to as: covered stent 200) is delivered to the aortic arch by using a stent delivery sheath tube 53 through a common iliac artery, an abdominal aorta, a thoracic aorta and a descending aorta. The release position of the covered stent 200 is adjusted to allow the covered stent 200 to be approximately located between the left subclavian artery 410a and a left common carotid artery 410b, and the covered stent 200 is partially released, and at the moment, the coating membrane of the covered stent 200 covers the blood inflow end of the left subclavian artery 410a. In the surgical procedure of the present embodiment, the coating membrane of the covered stent 200 may temporarily cover the blood inflow end of the left subclavian artery 410a.

It can be understood that in other surgical procedures, continuous blood supply of a branch vessel (such as the left subclavian artery 410a or the left common carotid artery 410b) may be maintained by using a transferring tube, as required. During the placement of the transferring tube, the femoral artery on the other side is punctured at first, and the transferring tube is placed into the branch vessel of the aortic arch; and then the covered stent 200 is partially released. In this way, the branch vessel still may maintain continuous blood supply under the action of the transferring tube.

Second step: outside the body of the patient, the push rod 13 and the puncturing needle 11 at the distal end of the push rod 13 are threaded through the accommodating cavity 211 of the catheter 21, and the puncturing needle 11 is threaded out from the anchoring balloon 22 (not filled). The catheter seat 23 and the handle 12 are in threaded connection through the fastener 15 arranged at the distal end of the distal end handle part 122. It can be understood that in other embodiments, the second step also may be completed before the first step.

Figure 8B:
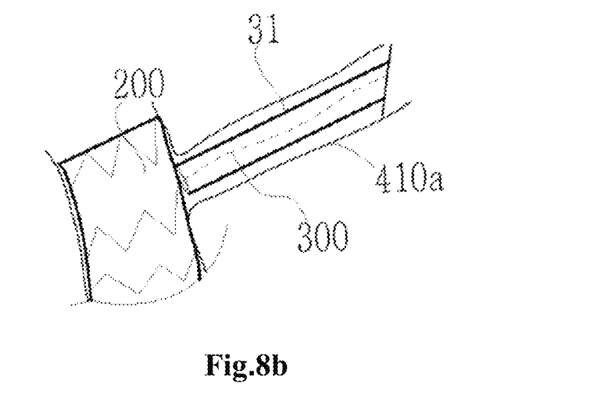
FIG. 8b is a schematic diagram of putting a guide wire into the left subclavian artery and delivering the delivery sheath tube along the guide wire till the distal end of the delivery sheath tube is in contact with a coating membrane of the covered stent.

Third step: referring to FIG. 8b, the guide wire 300 is put into the left subclavian artery 410a through brachial artery puncturing, and the delivery sheath tube 31 of the delivery assembly 30 is delivered along the guide wire 300 till the distal end of the delivery sheath tube 31 is in contact with the coating membrane of the covered stent 200.

Fourth step: the distal end of the catheter 21 (in which the push rod 13 is arranged in the penetrating manner) and the anchoring balloon 22 (in which the puncturing needle 11 is arranged in the penetrating manner) arranged at the distal end of the catheter 21 are moved to the distal end of the tube cavity of the delivery sheath tube 31 along the guide wire 300 to form the puncturing device 100.

Fifth step: the covered stent 200 is completely released.

Figure 8C:
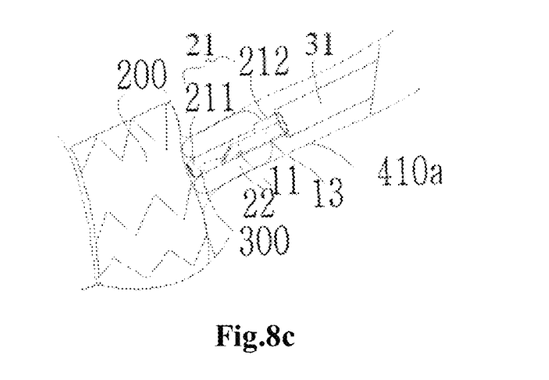
FIG. 8c is a schematic diagram of filling the anchoring balloon to cling to the vascular wall of the left subclavian artery after the anchoring balloon extends out of the delivery sheath tube.

Sixth step: referring now to FIG. 8c, the delivery sheath tube 31 is pulled back to allow the anchoring balloon 22 to completely extend out of the distal end of the tube cavity of the delivery sheath tube 31. The filling cavity 212 is connected with the external pressure device (such as a balloon expansion pressure pump, not shown in the figure) through the filling port 232 of the catheter seat 23. The liquid medium in the external pressure device enters the anchoring balloon 22 through the filling port 232 and the filling cavity 212 to expand the anchoring balloon 22, and the expanded anchoring balloon 22 clings to the vascular wall of the left subclavian artery 410a. Therefore, the expanded anchoring balloon 22 may restrain the catheter 21, the push rod 13 located in the accommodating cavity 211 of the catheter 21 and the puncturing needle 11 connected with the push rod 13 from moving radially. The annular end face of the distal end of the anchoring balloon 22 abuts against the coating membrane at the point to be punctured of the covered stent 200, and the coating membrane is pressed to form a tension region to be punctured.

Figure 8D:
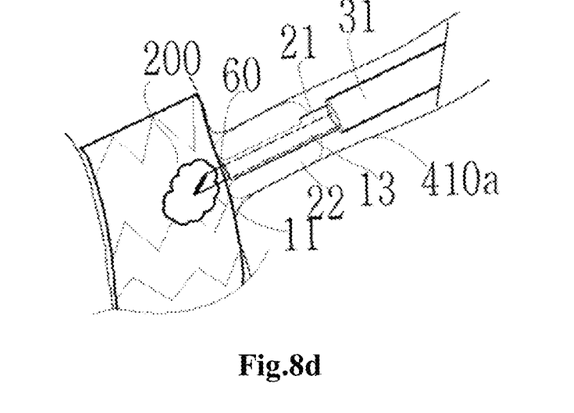
FIG. 8d is a schematic diagram of puncturing the coating membrane at a point to be punctured of the thoracic aorta covered stent through the puncturing needle.

Seventh step: the guide wire 300 is pulled back to be accommodated in the inner cavities of the puncturing needle 11 and the push rod 13. By maintaining the position of the distal end handle part 122 unchanged, the proximal end handle part 121 is quickly pushed towards the distal end to drive the puncturing needle 11 to puncture the coating membrane of the covered stent 200. Referring to FIG. 8d, a puncturing hole 60 is formed in the coating membrane at the moment.

Figure 8E:
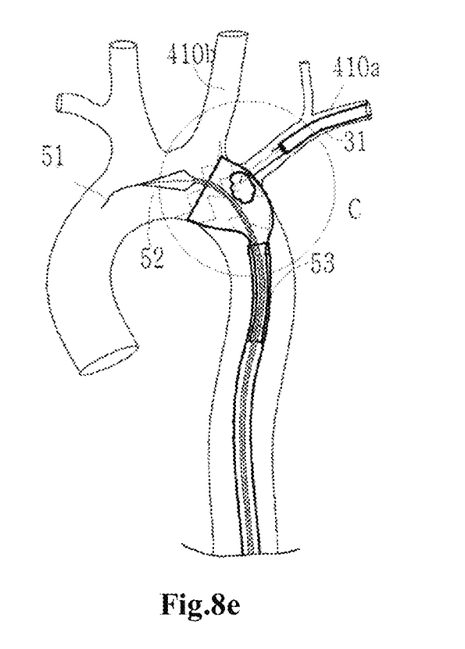
FIG. 8e is a schematic diagram of allowing the guide wire to be threaded out along an inner cavity of the puncturing needle and enter an inner cavity of the thoracic aorta covered stent.
Figure 8F:
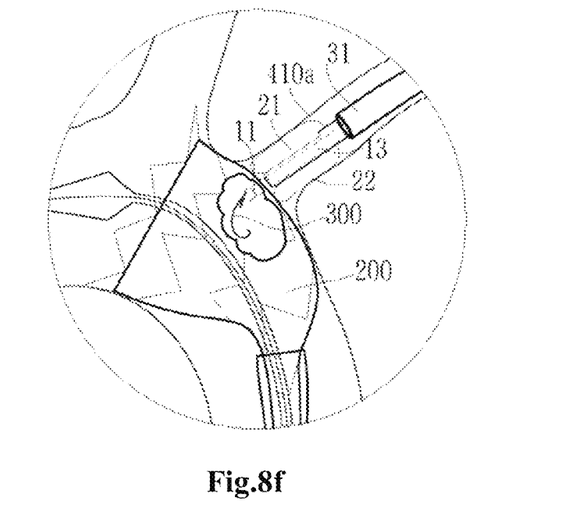
FIG. 8f is a partially enlarged view of the position C in FIG. 8e.

Eighth step: referring to FIG. 8e and FIG. 8f together, by maintaining the position of the puncturing needle 11 unchanged, the distal end of the guide wire 300 is pushed into the inner cavity of the covered stent 200 through the puncturing hole 60 formed in the seventh step along the inner cavities of the puncturing needle 11 and the push rod 13.

Figure 8G:
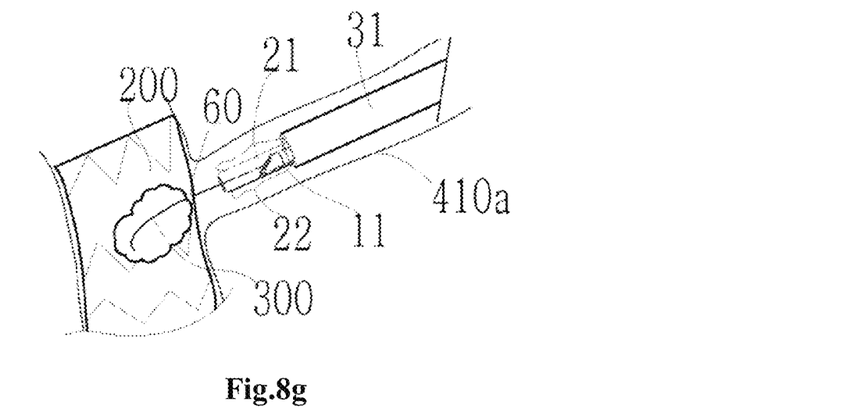
FIG. 8g is a schematic diagram of by maintaining the guide wire at the original position, withdrawing the puncturing needle and the push rod into the delivery sheath tube, and deflating and withdrawing the anchoring balloon.

Ninth step: referring to FIG. 8g, by maintaining the position of the guide wire 300 unchanged, the puncturing needle 11 is pulled back through the puncturing hole 60 so as to be removed from the inner cavity of the covered stent 200, and then the anchoring balloon 22 is deflated by using the external pressure device.

Figure 8H:
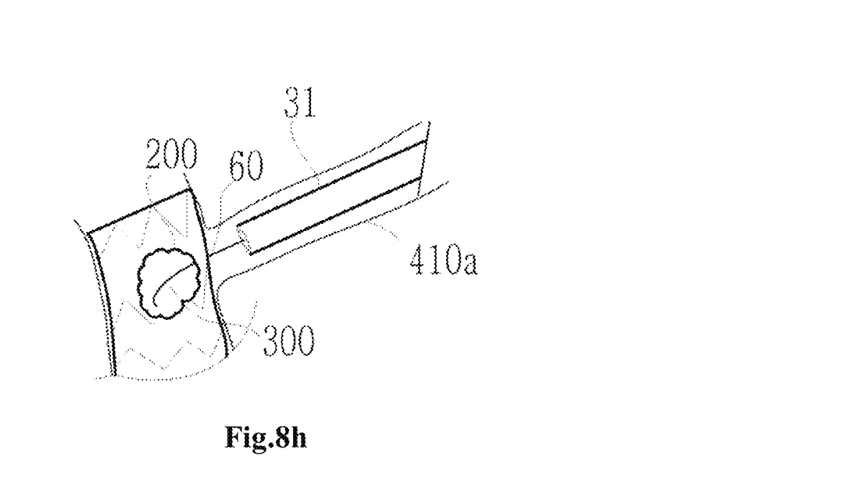
FIG. 8h is a schematic diagram of by maintaining the guide wire at the original position, withdrawing the anchoring balloon, the catheter, the puncturing needle and the push rod and building a delivery track for an expansion balloon and a branch stent.

Tenth step: referring to FIG. 8h, the catheter 21 (in which the push rod 13 is arranged in the penetrating manner) and the anchoring balloon 22 (in which the puncturing needle 11 is arranged in the penetrating manner) are withdrawn, and the delivery sheath tube 31 and the guide wire 300 are retained in the body of the patient, and at the moment, a track used for delivering an expansion balloon 40 (referring to FIG. 8i) and a branch stent (not shown in the figure) is built between the brachial artery puncturing point and the puncturing hole 60.

Figure 8I:
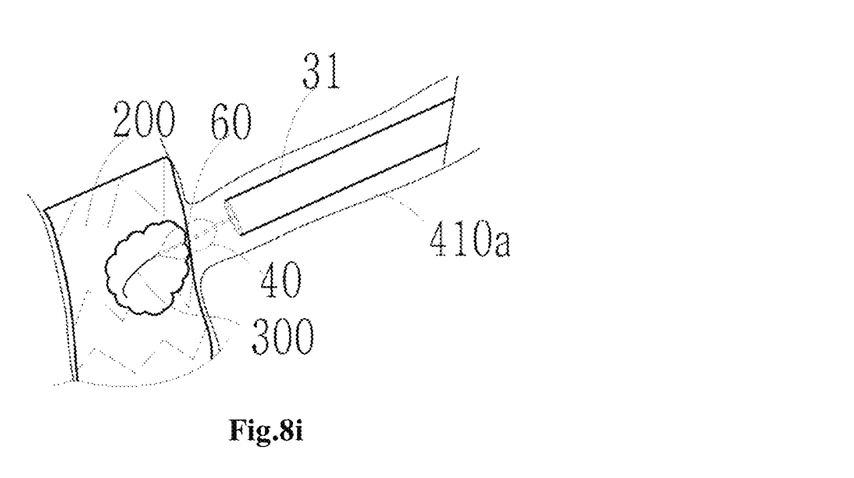
FIG. 8i is a schematic diagram of by maintaining the guide wire at the original position, delivering the expansion balloon along the guide wire to a puncturing hole for expansion and fenestration.

Eleventh step: referring to FIG. 8i, the expansion balloon 40 is delivered to the puncturing hole 60 through the delivery sheath tube 31 along the guide wire 300 by using the track built in the tenth step, and then is gradually filled to enlarge the area of the puncturing hole 60 to implement the in-situ fenestration of the covered stent 200.

In conclusion, according to the puncturing device provided by the present application, the distal end of the puncturing assembly is fixed by using the anchoring assembly, and the anchoring assembly is filled to cling to the vascular wall to restrain the radial movement of the distal end of the puncturing needle, so that the puncturing accuracy and success rate are improved.

According to the puncturing device provided by the present application, the puncturing needle and the push rod of the puncturing device are both hollow structures having the inner cavities, and the inner cavities of the puncturing needle and the push rod may be used as guide wire channels. After the puncturing is completed, only the puncturing assembly and the anchoring assembly are required to be withdrawn, and the delivery sheath tube and the guide wire are retained in the body, so as to build the delivery channel for the expansion balloon and the branch stent without redoing the guide wire to search a puncturing port. Furthermore, the guide wire is movably arranged in the inner cavities of the puncturing needle and the push rod in the penetrating manner to reduce the number of expander components in the prior art and decrease the outer diameter of the delivery assembly, so that the delivery assembly may successfully pass through a blood vessel having a relatively small inner diameter and also may lower the damage of the device to the blood vessel.

According to the anchoring device provided by the present application, the central region of the distal end part of the anchoring balloon of the anchoring device has the sunken region sunken from the distal end to the proximal end and surrounding the distal end of the catheter. After the anchoring balloon is filled to expand, the distal end face of the anchoring balloon is the annular end face surrounding the catheter. In the puncturing process, after the anchoring balloon is filled to expand in the target blood vessel, the annular end face abuts against the coating membrane of the punctured stent, and the elastic coating membrane is stressed by the pull force to form the tension region surrounded by the annular end face of the anchoring balloon. After the puncturing needle is threaded out from the distal end of the anchoring balloon and in contact with the coating membrane of this tension region, the coating membrane of the tension region is directly punctured by the puncturing needle instead of being sunken into the covered stent, so that the puncturing success rate is increased. In addition, as the coating membrane in the tension region may not be sunken into the covered stent, the distance between the distal end of the puncturing needle and the contralateral coating membrane and the distance between the distal end of the puncturing needle and the vascular wall are prolonged, and then the possibility that the puncturing needle continuously moves forwards after making a puncturing success to puncture the contralateral coating membrane or the vascular wall because of an extremely high puncturing force is reduced.

In the present application, the semi-compliable balloon is used as the anchoring balloon. After arriving at the point to be punctured, the part, close to the distal end and covered by the anchoring balloon, of the catheter may bend under the impact of the filled anchoring balloon with the increase of the pressure in the anchoring balloon, so as to better comply with the bent anatomical structure of the blood vessel.

The push rod of the present application is of the spiral tubular structure twisted by a single, or multiple wires, is high in flexibility and may comply with a complicated and twisted anatomical structure. The length of the puncturing needle is less than or equal to 7 mm, so that the pass-ability in the blood vessel is high, and damage caused by the puncturing needle to surrounding blood vessels is reduced.

The puncturing handle of the present application is suitable for one-handed operation. The proximal end handle shaft may be driven to axially move relative to the distal end handle shaft through opening and closing of an index finger and a thumb of one hand to drive the push rod and the puncturing needle to implement puncturing as long as the distal end handle ring and the proximal end handle ring are respectively operated with the index finger and the thumb of one hand, and the operation is convenient and quick.

After the puncturing device and the anchoring device which are provided by the present application are adopted to carry out the puncturing, expansion balloons or cutting balloons of different specifications may be selected as required, so as to expand the puncturing point to an expected fenestration size. In the expansion process, the expansion force is along the radial direction of the expansion balloon, so the defects of a limited expansion size of a tapered expander adopted in the prior art, stent displacement caused by the expander and the like are overcome.

It can be understood that the in-situ fenestration of the covered stent above is only one use of the puncturing device and the anchoring device which are provided by the present application, and the puncturing device and the anchoring device which are provided by the present application also may be applied to puncturing a blood vessel, a trachea, or other lumens in a human body, or applied to returning into a true lumen in the surgery, as desired.

The above-mentioned contents are only exemplary embodiments of the present application, and are not intended to limit the present application. Any modifications, equivalent replacements, improvements and the like that are made within the spirit and the principle of the present application shall all fall within the protection scope of the present application.

The invention claimed is:

1. A puncturing device, comprising: a puncturing needle, an inflatable anchoring balloon, and a catheter passing through a proximal end and a distal end of the anchoring balloon, the puncturing needle being movably arranged in the catheter; wherein, in a filled state, a central region of the distal end part of the anchoring balloon is sunken towards the proximal end of the anchoring balloon to form a sunken region, and a distal end of the catheter is located in the sunken region, the radial movement of the catheter and the puncturing needle are limited by the anchoring balloon in the filled state, wherein the distal end of the anchoring balloon is flush with the distal end of the catheter, or the distal end of the anchoring balloon extends out of the distal end of the catheter by less than or equal to 2 mm along the axial direction of the catheter.

2. The puncturing device according to claim 1, wherein the anchoring balloon has an axial length that ranges between 5 mm and 20 mm.

3. The puncturing device according to claim 1, wherein the catheter is a multi-cavity tube having at least two cavities; the multi-cavity tube comprises an accommodating cavity and a filling cavity; the accommodating cavity axially passes through the anchoring balloon, and the puncturing needle is movably accommodated in the accommodating cavity; and a distal end of the filling cavity is accommodated in the anchoring balloon, and a tube cavity of the filling cavity is communicated with an inside of the anchoring balloon.

4. The puncturing device according to claim 3, wherein a hardness of a part, covered by the anchoring balloon, of the catheter is lower than that of the other part of the catheter.

5. The puncturing device according to claim 1, wherein a length of the needle tip of the puncturing needle is less than or equal to 7 mm.

6. The puncturing device according to claim 1, wherein, in a filled state, the central region of the distal end part of the anchoring balloon is sunken towards the proximal end of the anchoring balloon to form the sunken region, and the distal end of the catheter is located in the sunken region, such that the distal end part of the anchoring balloon presses against a punctured site, thereby forming a tensioned area to be punctured at the punctured site.

7. A puncturing device, comprising: a puncturing needle, an inflatable anchoring balloon, and a catheter passing through a proximal end and a distal end of the anchoring balloon, the puncturing needle being movably arranged in the catheter; wherein, in a filled state, a central region of the distal end part of the anchoring balloon is sunken towards the proximal end of the anchoring balloon to form a sunken region, and a distal end of the catheter is located in the sunken region, wherein the puncturing device further comprises a handle connected with the puncturing needle; the handle comprises a proximal end handle part and a distal end handle part which are opposite to each other; the proximal end handle part comprises a proximal end handle shaft having an axial inner cavity and a proximal end handle ring connected to a side wall of the proximal end handle shaft; the axial inner cavity of the proximal end handle shaft passes through a proximal end face and a distal end face of the proximal end handle shaft; the distal end handle part comprises a distal end handle shaft having an axial inner cavity and a distal end handle ring connected to a side wall of the distal end handle shaft; the axial inner cavity of the distal end handle shaft passes through a proximal end face and a distal end face of the distal end handle shaft; and the proximal end handle shaft is movably arranged in the axial inner cavity of the distal end handle shaft in a penetrating manner, and the distal end handle ring is closer to a proximal end of the puncturing needle than the proximal end handle ring.

8. The puncturing device according to claim 7, wherein an outer profile of the part, accommodated in the axial inner cavity of the distal end handle shaft, of the proximal end handle shaft on a section perpendicular to an axial direction of the proximal end handle shaft is noncircular.

9. The puncturing device according to claim 7, wherein the handle further comprises a fastener arranged at a distal end of the distal end handle shaft and connected with a proximal end of the anchoring assembly.

10. The puncturing device according to claim 7, wherein the puncturing device further comprises a push rod connected between the puncturing needle and the handle, and a proximal end of the push rod is fixedly accommodated in the axial inner cavity of the proximal end handle shaft.

11. The puncturing device according to claim 10, wherein the push rod further comprises a reinforcing tube arranged on the push rod; the reinforcing tube is arranged on a rod-like part, close to the proximal end of the push rod, of the push rod in a sleeving manner, and a hardness of the reinforcing tube is higher than that of the rod-like part, close to the proximal end of the push rod, of the push rod.

12. The puncturing device according to claim 11, wherein an axial length of the reinforcing tube is less than or equal to ⅓ of an axial length of the push rod.

13. An anchoring device, comprising: an inflatable anchoring balloon and a catheter that passes through a proximal end and a distal end of the anchoring balloon, wherein, in a filled state, a central region of the distal end part of the anchoring balloon is sunken towards the proximal end of the anchoring balloon to form a sunken region, and a distal end of the catheter is located in the sunken region, the radial movement of the catheter and the puncturing needle are limited by the anchoring balloon in the filled state, wherein the distal end of the anchoring balloon is flush with the distal end of the catheter, or the distal end of the anchoring balloon extends out of the distal end of the catheter by less than or equal to 2 mm along the axial direction of the catheter.

14. The anchoring device according to claim 13, wherein the anchoring balloon has an axial length that ranges between 5 mm and 20 mm.

15. The anchoring device according to claim 13, wherein a hardness of a part, covered by the anchoring balloon, of the catheter is lower than that of the other part of the catheter.

16. The anchoring device according to claim 13, wherein, in a filled state, the central region of the distal end part of the anchoring balloon is sunken towards the proximal end of the anchoring balloon to form the sunken region, and the distal end of the catheter is located in the sunken region, such that the distal end part of the anchoring balloon presses against a punctured site, thereby forming a tensioned area to be punctured at the punctured site.

* * * * *